(12) United States Patent
Rezaee et al.

(10) Patent No.: US 9,454,814 B2
(45) Date of Patent: Sep. 27, 2016

(54) PACS VIEWER AND A METHOD FOR IDENTIFYING PATIENT ORIENTATION

(71) Applicant: McKesson Financial Holdings, Hamilton (BM)

(72) Inventors: Mahmoud Ramze Rezaee, North Vancouver (CA); Darya Abdollahzadeh, Vancouver (CA); Delaram Behnami, North Vancouver (CA); Ava Sheikhi Shoshtari, West Vancouver (CA); Purang Abolmaesumi, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 9 days.

(21) Appl. No.: 14/606,609

(22) Filed: Jan. 27, 2015

(65) Prior Publication Data
US 2016/0217564 A1    Jul. 28, 2016

(51) Int. Cl.
| | |
|---|---|
| *G06K 9/00* | (2006.01) |
| *G06T 7/00* | (2006.01) |
| *G06K 9/46* | (2006.01) |
| *G06K 9/62* | (2006.01) |

(52) U.S. Cl.
CPC ........... *G06T 7/0012* (2013.01); *G06K 9/4604* (2013.01); *G06K 9/6215* (2013.01); *G06K 9/6267* (2013.01); *G06T 7/0044* (2013.01); *G06T 7/0079* (2013.01); *G06T 2207/20112* (2013.01); *G06T 2207/30061* (2013.01)

(58) Field of Classification Search
USPC ....................................................... 382/128
See application file for complete search history.

(56) References Cited

U.S. PATENT DOCUMENTS

| | | | | |
|---|---|---|---|---|
| 7,756,316 B2 * | 7/2010 | Odry | .................... | G06K 9/4638 382/131 |
| 7,912,263 B2 * | 3/2011 | Luo | ........................ | G06T 7/0012 378/37 |
| 8,401,285 B1 * | 3/2013 | Rezaee | ........................ | 382/128 |
| 2003/0099385 A1 * | 5/2003 | Zeng | ..................... | G06T 7/0012 382/128 |
| 2005/0207630 A1 * | 9/2005 | Chan | ..................... | A61B 6/466 382/131 |
| 2009/0041324 A1 * | 2/2009 | Yamagata | ............. | G06F 19/321 382/131 |

(Continued)

OTHER PUBLICATIONS

Armato, S. G. III et al., *Automated Lung Segmentation in Digitized Posteroanterior Chest Radiographs*, Academic Radiology 5 (4) (1998) 245-255.

(Continued)

*Primary Examiner* — John Strege
(74) *Attorney, Agent, or Firm* — Alston & Bird LLP

(57) ABSTRACT

A PACS viewer and an associated method and computer program product are provided for identifying patient orientation. With respect to a PACS viewer, the PACS viewer includes processing circuitry configured to register an image onto a template. The processing circuitry is also configured to determine a representative seed point within each of the left and right lungs as represented by the image. The processing circuitry is further configured to apply an active contour model to each of the left and right lungs to generate a binary image of the left and right lungs. In this regard, the processing circuitry is configured to apply the active contour model by initializing the active contour model with a mask constructed using the representative seed points. Further, the processing circuitry is configured to detect at least one feature from the binary image to permit identification of the left and right lungs.

20 Claims, 14 Drawing Sheets

(56) References Cited

U.S. PATENT DOCUMENTS

2015/0005659 A1* 1/2015 Masumoto .............. A61B 6/032
600/538
2015/0310172 A1* 10/2015 Takata .................. G06F 19/321
382/128

OTHER PUBLICATIONS

Burges, C. J. C., *A Tutorial on Support Vector Machines for Pattern Recognition*, Data Mining and Knowledge Discovery, 2 (1998), 121-167.

Chan, T. F. et al., *Active Contours Without Edges*, IEEE Transactions on Image Processing 10(2) (Feb. 2001) 266-277.

Chang, C. C. et al., *LIBSVM: A Library for Support Vector Machines*, ACM Translation on Intelligent Systems and Technology, vol. 2, No. 3 (Apr. 2011) 1-27.

Iakovidis, D. K. et al., *Automatic Segmentation of the Lung Fields in Portable Chest Radiographs Based on Bézier Interpolation of Salient Control Points*, IEEE International Workshop on Imaging Systems and Techniques, Ist 2008 (Sep. 2008) 1-6.

Joshi, S. et al., *Unbiased Diffeomorphic Atlas Construction for Computational Anatomy*, NeuroImage 23 (Sep. 2004) S151-S160.

Le, K., *Chest X-ray Analysis for an Active Distributed E-Health System with Computer-Aided Diagnosis*, Computer Sciences and Convergence Information Technology (ICCIT), 2010 $5^{th}$ International Conference (Dec. 2010) 727-732.

Platt, J. M. et al., *The Application of Anatomical Side Markers During Abdominal and IVU Examination: An Investigation of Practice Prior to and Post-Installation of Computed Radiography (CR)*, The College of Radiographers 15(4) (Nov. 2009) pp. 292-299.

Sohn, K., *Segmentation of Lung Fields Using Chan-Vese Active Contour Model in Chest Radiographs*, Computer-Aided Diagnosis, 796332 (Mar. 2011) 1-9.

Xu, T. et al., *Gradient Vector Flow Based Active Shape Model for Lung Field Segmentation in Chest Radiographs*, Engineering in Medicine and Biology Society, Annual International Conference of the IEEE (2009) 3561-3564.

\* cited by examiner

PACS VIEWER AND A METHOD FOR IDENTIFYING PATIENT ORIENTATION

TECHNOLOGICAL FIELD

An example embodiment relates generally to a picture archiving and communications system (PACS) viewer and associated method and, more particularly, to a PACS viewer and associated method for identifying patient orientation.

BACKGROUND

Images of a patient are captured with a wide range of modalities including, for example, computerized tomography (CT), magnetic resonance imaging (MRI), computed radiography (CR), digital radiography (DR) and mammography (MG). In order to properly assess the image and to subsequently treat the patient based upon information gathered from the image, the orientation of the patient at the time that the image was captured is of import. By determining the orientation of the patient, specific features of the patient are able to be identified as being either on the left side or on the right side of the patient. For example, the left lung may be distinguished from the right lung such that any subsequent treatment of the patient to address a lung condition that exists in only one of the lungs is focused upon the correct lung.

The orientation of the patient may be identified in various manners. In one example, a technician may place a designation, such as an L or an R, on or proximate to the patient so as to designate the left side or the right side of the patient, respectively. The designation will be captured within the image and will provide an indication to technicians, radiologists or other healthcare practitioners who subsequently review the image study as to the orientation of the patient. Alternatively, following the capture of an image, a technician may insert a designation into the image itself, such as by burning an L or an R designating left side or right side of the patient, respectively, into the image. By inserting the designation into the image, a technician, a radiologist or other healthcare practitioner who reviews the image study will be able to determine the orientation of the patient at the time that the image was captured. Still further, an indication may be inserted into the header of a medical image study that indicates the orientation of the patient at the time that the image was captured. The indication that is inserted into the header may be based upon a predefined protocol in which the patient is assumed to be in a particular orientation at the time that the image was captured. For example in posteroanterior (PA) chest exams in computed radiography, the imaging plate is placed in front of the patient with the x-ray beam originates from behind the patient. This arrangement results in an image in which the left side of the patient is displayed on the right side of the image as if the patient is standing in front of the physician.

While the foregoing techniques are useful in identifying the orientation of a patient at the time that an image was captured, in instances in which a designation is to be associated with the image, a technician may sometimes forget to place a designation proximate the patient at the time that an image is captured or may forget to burn a designation into the image. As such, it may be difficult to determine the orientation of the patient during subsequent review of the medical image study, at least with the degree of accuracy that is desired. Alternatively, in instances in which an indication of the orientation is to be inserted into the head of an image study, the patient may not be oriented in accordance with the predefined protocol at the time that image is captured such that the resulting designation of the orientation that is included within the header of the medical image study will correspondingly be inaccurate with such inaccuracies potentially leading to undesired issues associated with the subsequent treatment of the patient based upon a review of the medical image study.

BRIEF SUMMARY

A PACS viewer and an associated method and computer program product are provided in accordance with an example embodiment for identifying patient orientation in a reliable and automated manner. For example, the PACS viewer and associated method and computer program product of an example embodiment are configured to discriminate between the left and right lungs of a patient based upon an image of the patient without reliance upon placement of a designation proximate the patient at the time that the image was captured, burning a designation into an image or orientation of the patient at the time of image capture according to a predefined protocol. As such, the PACS viewer and associated method and computer program product offer reliable identification of the left and right lungs of a patient while providing greater freedom in terms of the orientation of the patient at the time that the image is captured. By reliably identifying the left and right lungs of the patient from the image, the PACS viewer and associated method and computer program product may avoid issues associated with subsequent treatment of a patient based upon a medical image study in which the orientation of the patient was lacking or incorrect.

In an example embodiment, a PACS viewer is provided that includes processing circuitry configured to register an image onto a template. The processing circuitry is also configured to determine a representative seed point within each of the left and right lungs as represented by the image. The processing circuitry is further configured to apply an active contour model to each of the left and right lungs to generate a binary image of the left and right lungs. In this regard, the processing circuitry is configured to apply the active contour model by initializing the active contour model with a mask constructed using the representative seed points. Further, the processing circuitry of this example embodiment is configured to detect at least one feature from the binary image to permit identification of the left and right lungs.

The processing circuitry of an example embodiment is configured to detect at least one feature of the binary image by determining an area of the left and right lungs from the binary image and by identifying the right lung to have the larger area. The processing circuitry of another example embodiment is configured to detect at least one feature from the binary image by defining a line between left and right lungs as represented by the binary image. The line is located based upon a diaphragm of one of the lungs. The processing circuitry of this example embodiment is also configured to divide the line into first and second line segments extending between a midline between the left and right lungs and the respective lung. The processing circuitry of this example embodiment is further configured to compare the length of each of the first and second line segments and to identify the left lung to be on the same side of the midline as the longer of the first and second line segments. The processing circuitry of yet another example embodiment is configured to detect at least one feature from the binary image by making a first comparison of the binary image to the template and making a second comparison of a mirrored version of one of the binary image or the template to the other one of the binary image or the template. The template represents a predefined orientation with respect to the left and right lungs. The processing circuitry of this example embodiment also determines which of the first comparison or the second comparison is indicative of more similarity and identifies the left and right lungs within the binary image based upon the predefined orientation of the template and the one of the first or second comparison that is indicative of more similarity.

The processing circuitry of an example embodiment is configured to determine a representative seed point by defining a plurality of lines extending across the image and to determine, within each of the left and right lungs, a seed point on each of the plurality of lines. The processing circuitry of this example embodiment is also configured to determine the representative seed point within each of the left and right lungs from among the seed points determined on each of the plurality of lines within each of the left and right lungs. The processing circuitry of an example embodiment is further configured to subject the image to anisotropic diffusion prior to applying the active contour model. The processing circuitry of an example embodiment is also configured to predict patient orientation based upon the identification of the left and right lungs utilizing a support vector machine classifier. In this example embodiment, the processing circuitry is further configured to compare the patient orientation that is predicted to an indication of orientation that is associated with the image and to cause a notification to be provided in an instance in which the patient orientation that is predicted is different than the indication of orientation that is associated with the image.

In another example embodiment, a method for identifying patient orientation is provided that includes registering an image onto a template. The method also includes determining a representative seed point within each of the left and right lungs as represented by the image. The method further includes applying an active contour model to each of the left and right lungs to generate a binary image of the left and right lungs. In this regard, the method applies the active contour model by initializing the active contour model with a mask constructed using the representative seed points. The method of this example embodiment also includes detecting at least one feature from the binary image to permit identification of the left and right lungs.

The method of an example embodiment detects at least one feature from the binary image by determining an area of the left and right lungs from the binary image and by identifying the right lung to have the larger area. The method of another example embodiment detects at least one feature from the binary image by defining a line between the left and right lungs as represented by the binary image. The line is located based upon a diaphragm of one of the lungs. The method of this example embodiment also includes dividing the line into first and second line segments extending between a midline between the left and right lungs and a respective lung. The method of this embodiment further includes comparing a length of each of the first and second line segments and identifying the left lung to be on the same side of the midline as the longer of the first and second line segments. The method of another example embodiment detects at least one feature from the binary image by making a first comparison of the binary image to the template and making a second comparison of a mirrored version of one of the binary image or the template to the other one of the binary image or the template. The template represents a predefined orientation with respect to the left and right lungs. The method of this example embodiment also determines which of the first comparison or the second comparison is indicative of more similarity and identifies the left and right lungs within the binary image based upon the predefined orientation of the template and the one of the first or second comparison that is indicative of more similarity.

The method of an example embodiment determines a representative seed point by defining a plurality of lines extending across the image and determining, within each of the left and right lungs, a seed point on each of the plurality of lines. The method of this example embodiment also includes determining the representative seed point within each of the left and right lungs from among the seed points determined on each of the plurality of lines within each of the left and right lungs. The method of an example embodiment also includes subjecting the image to anisotropic diffusion prior to applying the active contour model. The method of an example embodiment also includes predicting patient orientation based upon the identification of the left and right lungs utilizing a support vector machine classifier. The method of this example embodiment also includes comparing the patient orientation that is predicted to an indication of orientation that is associated with the image and causing a notification to be providing in an instance in which the patient orientation that is predicted is different than the indication of orientation that is associated with the image.

In a further example embodiment, a computer program product is provided for identifying patient orientation. The computer program product includes a non-transitory computer readable storage medium having program code portions stored therein with the program code portions configured, upon execution, to register an image onto a template. The computer program product also includes program code portions configured to determine a representative seed point within each of the left and right lungs as represented by the image and program code portions configured to apply an active contour model to each of the left and right lungs to generate a binary image of the left and right lungs. In this regard, the program code portions configured to apply the active contour model include program code portions configured to initialize the active contour model with a mask constructed using the representative seed points. The computer program product of this example embodiment also includes program code portions configured to detect at least one feature from binary image to permit identification of the left and right lungs.

The program code portions configured to detect at least one feature from the binary image include, in an example embodiment, program code portions configured to determine an area of the left and right lungs from the binary image and program code portions configured to identify the right lung to have the larger area. In another example embodiment, the program code portions configured to detect at least one feature from the binary image includes program code portions configured to define a line between the left and right lungs as represented by the binary image. The line is located based upon a diaphragm of one or the lungs. The program code portions of this example embodiment are also configured to divide the line into first and second line segments extending between a midline between the left and right lungs and the respective lung. The program code portions of this example embodiment are further configured to compare a length of each of the first and second ling segments and to identify the left lung to be on the same side of the midline as the longer of the first and second line segments. In a further example embodiment, the program code portions configured to detect at least one feature from the binary image include program code portions configured to make a first comparison of the binary image to the template and to make a second comparison of a mirrored version of one of the binary image or the template to the other one of the binary image or the template. The template represents a predefined orientation with respect to the left and right lungs. In this example embodiment, the program code portions configured to detect at least one feature from the binary image also include program code portions configured to determine which of the first comparison or the second comparison is indicative of more similarity and program code portions configured to identify the left and right lungs within the binary image based upon the predefined orientation of the template and the one of the first or second comparison that is indicative of more similarity.

BRIEF DESCRIPTION OF THE DRAWINGS

Figure 1:
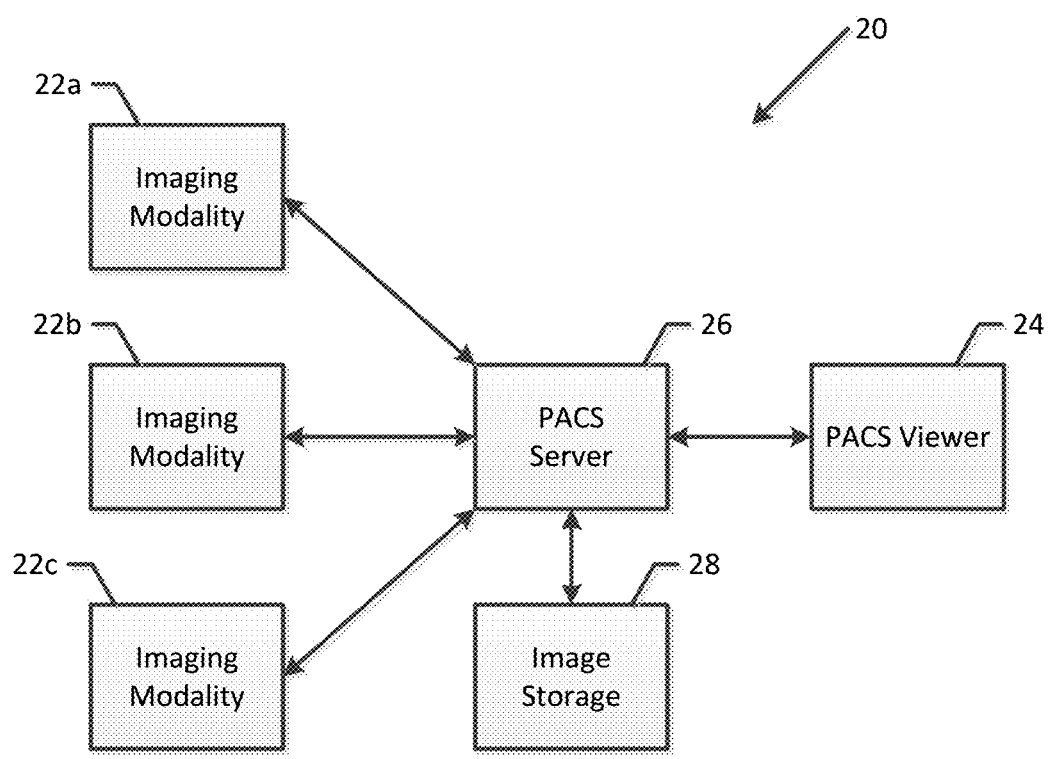
Figure 2:
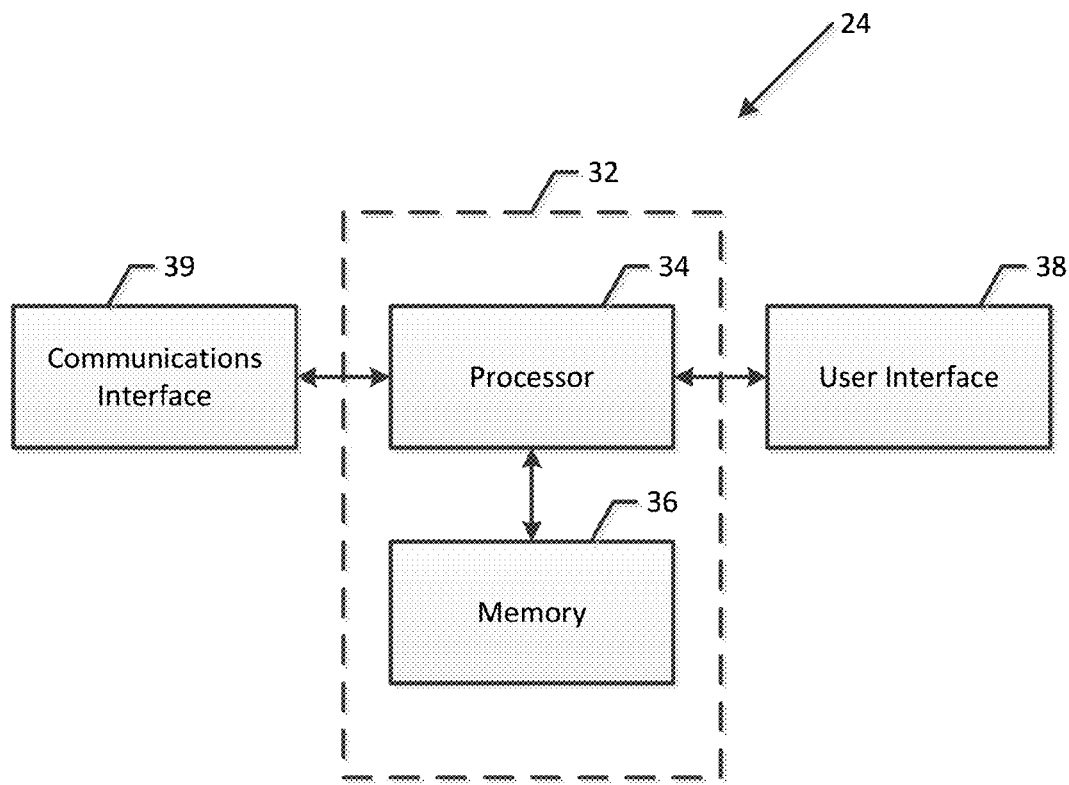
Figure 3:
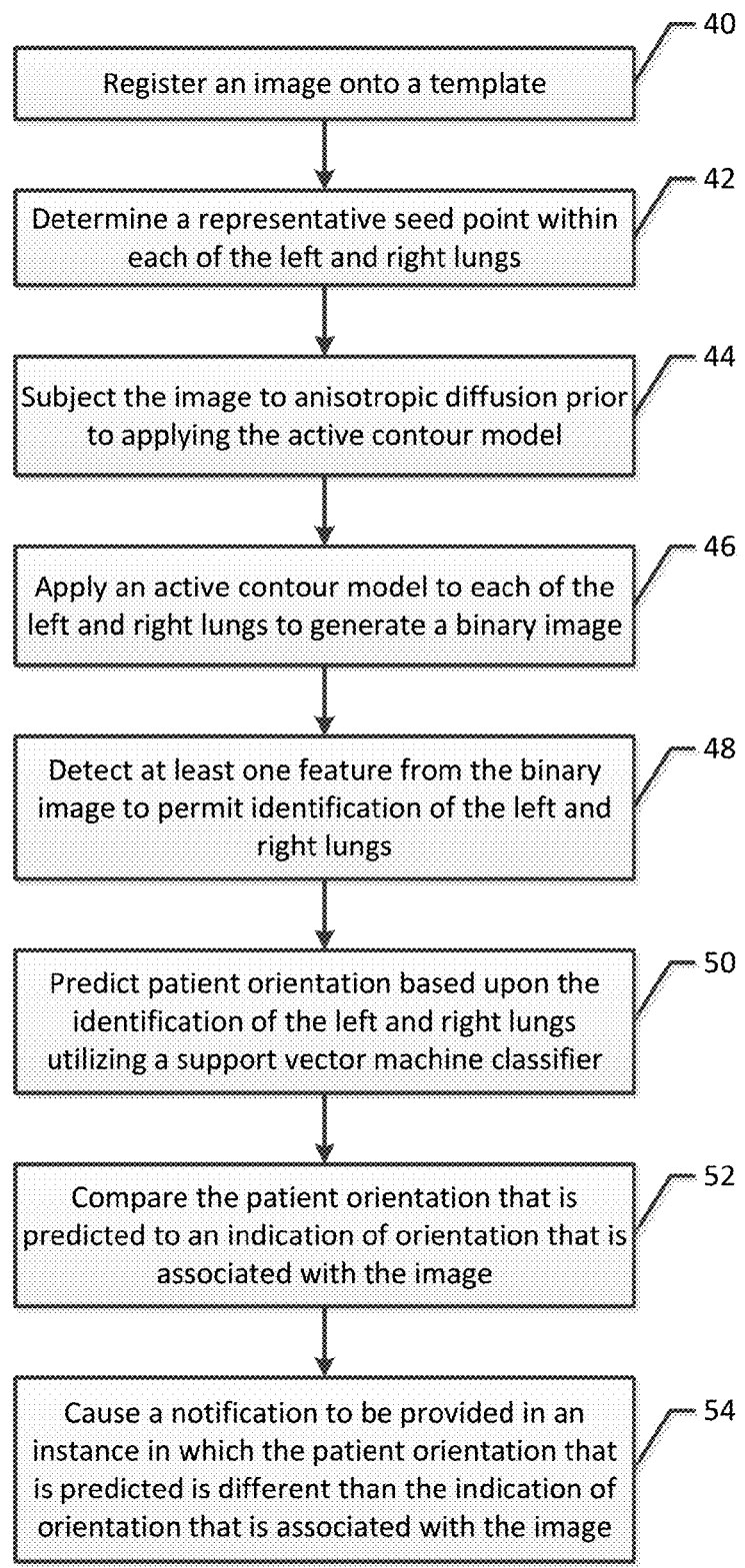
Figure 4:
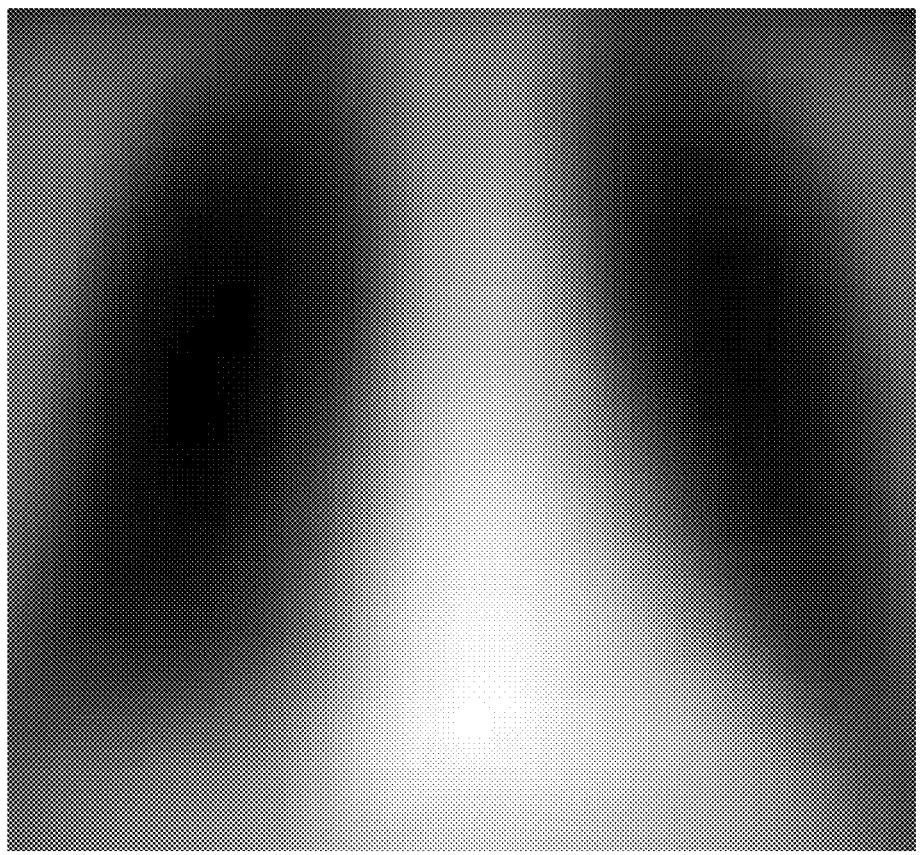
Figure 5:
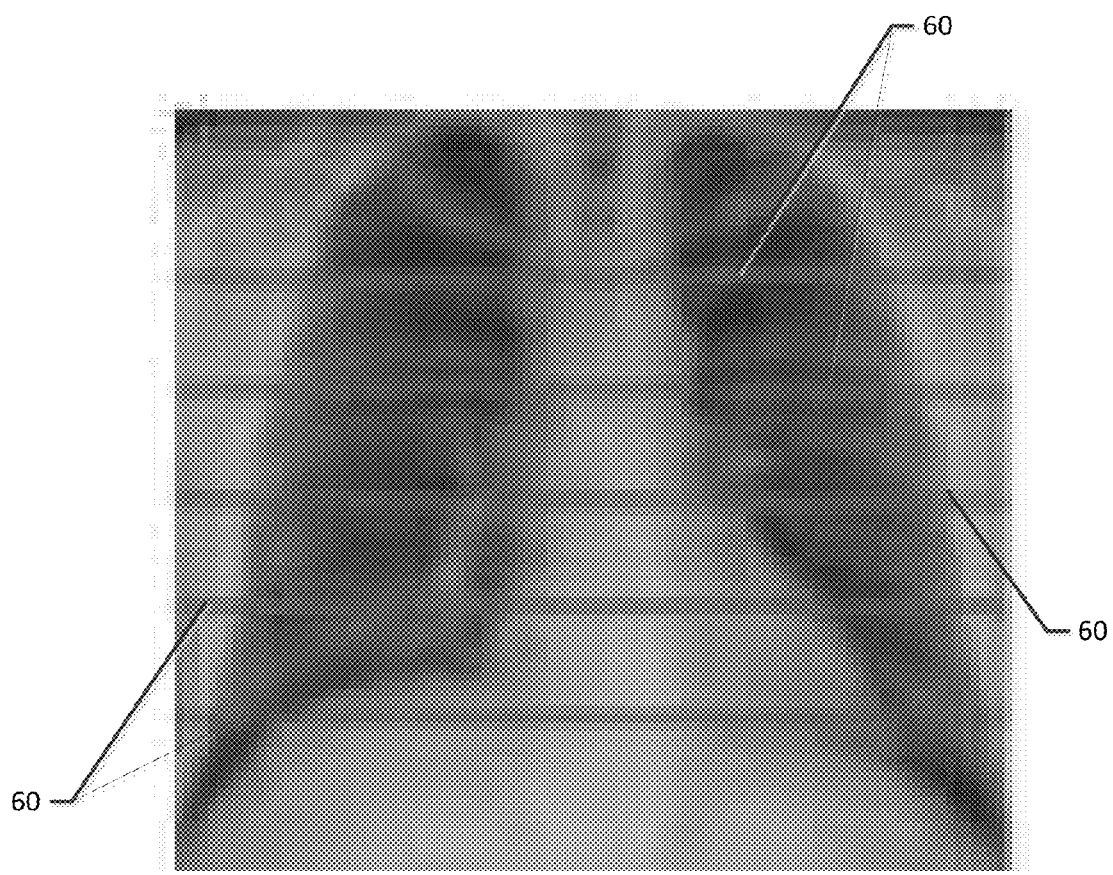
Figure 6:
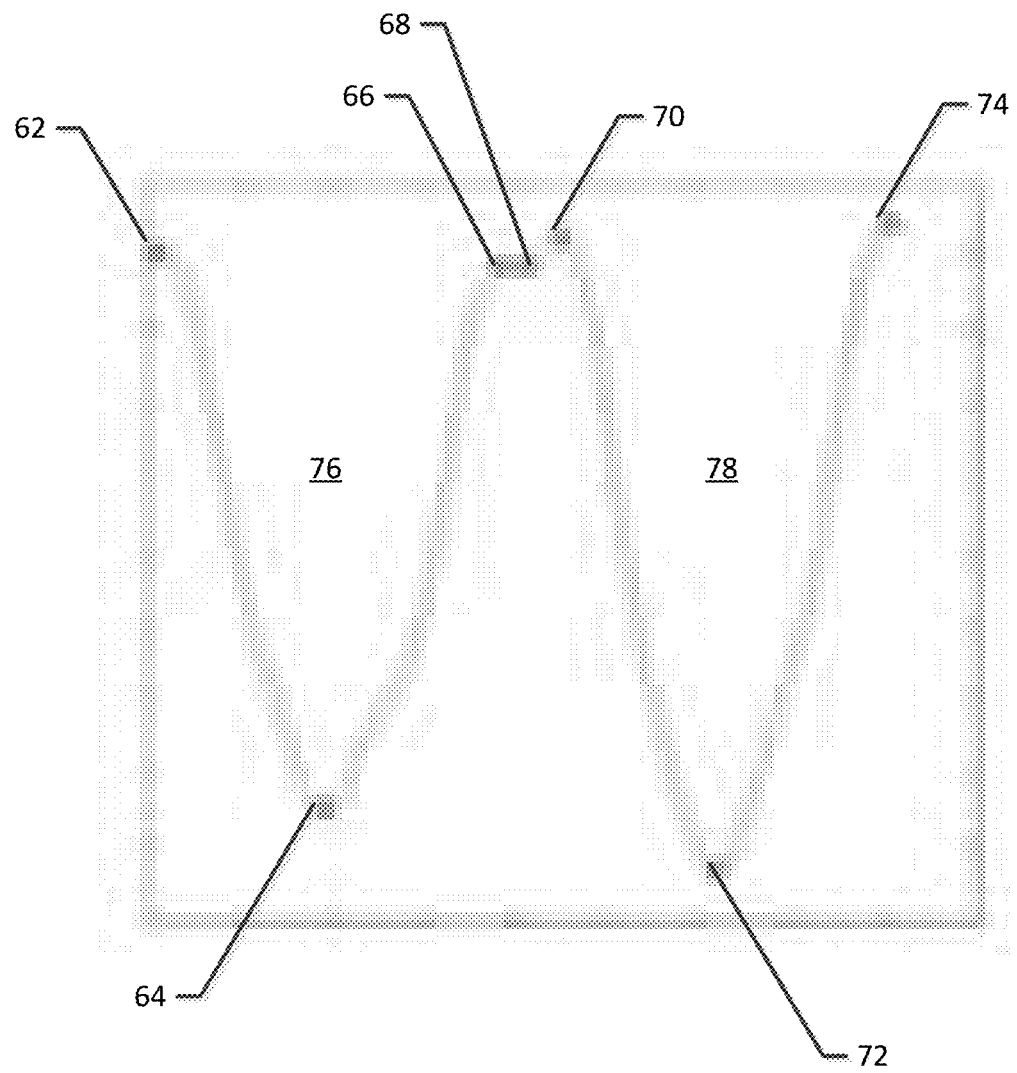
Figure 7:
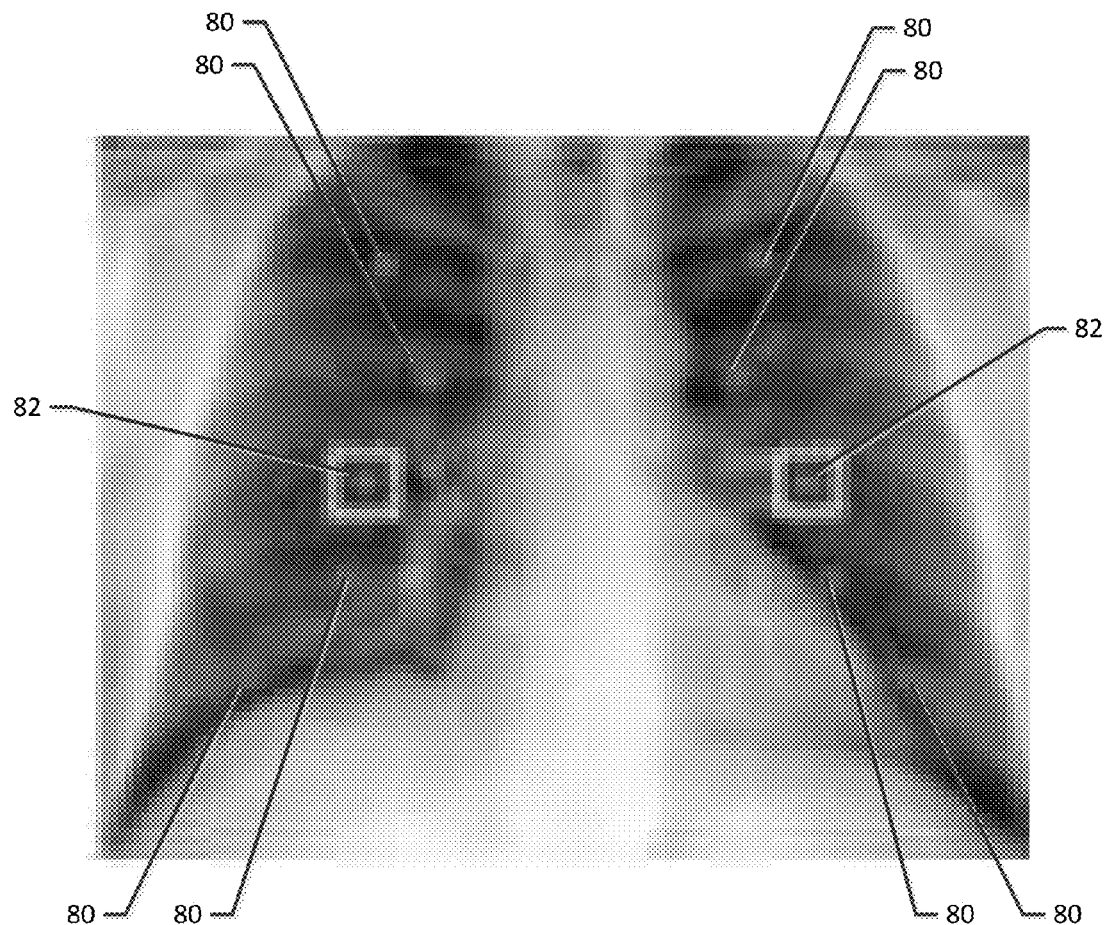
Figure 8:
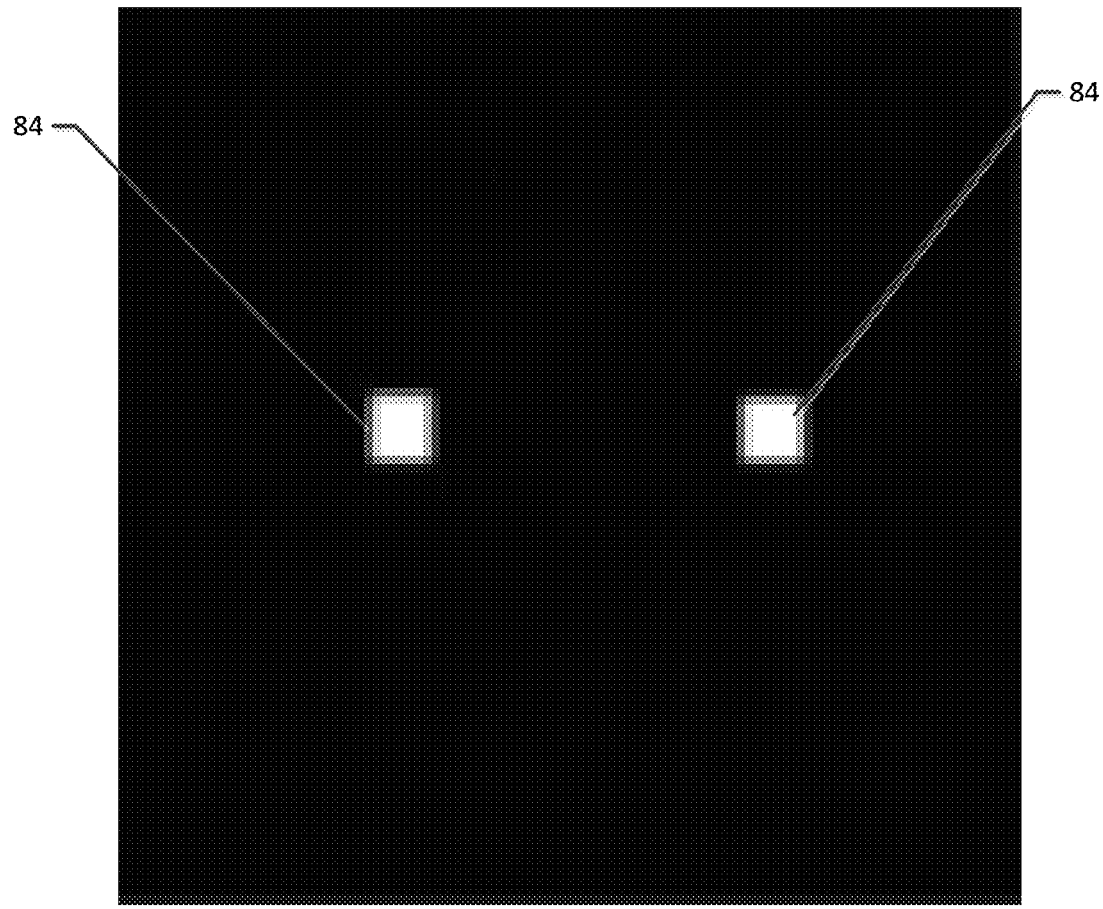
Figure 9:
Figure 10:
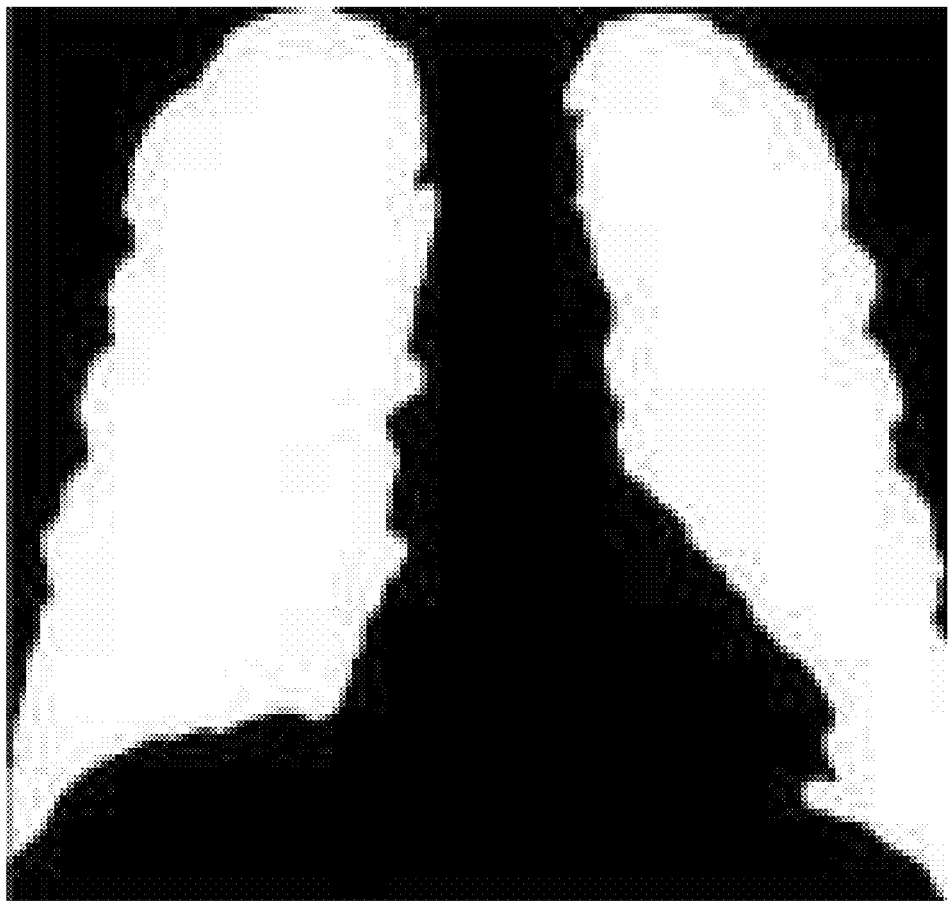
Figure 11:
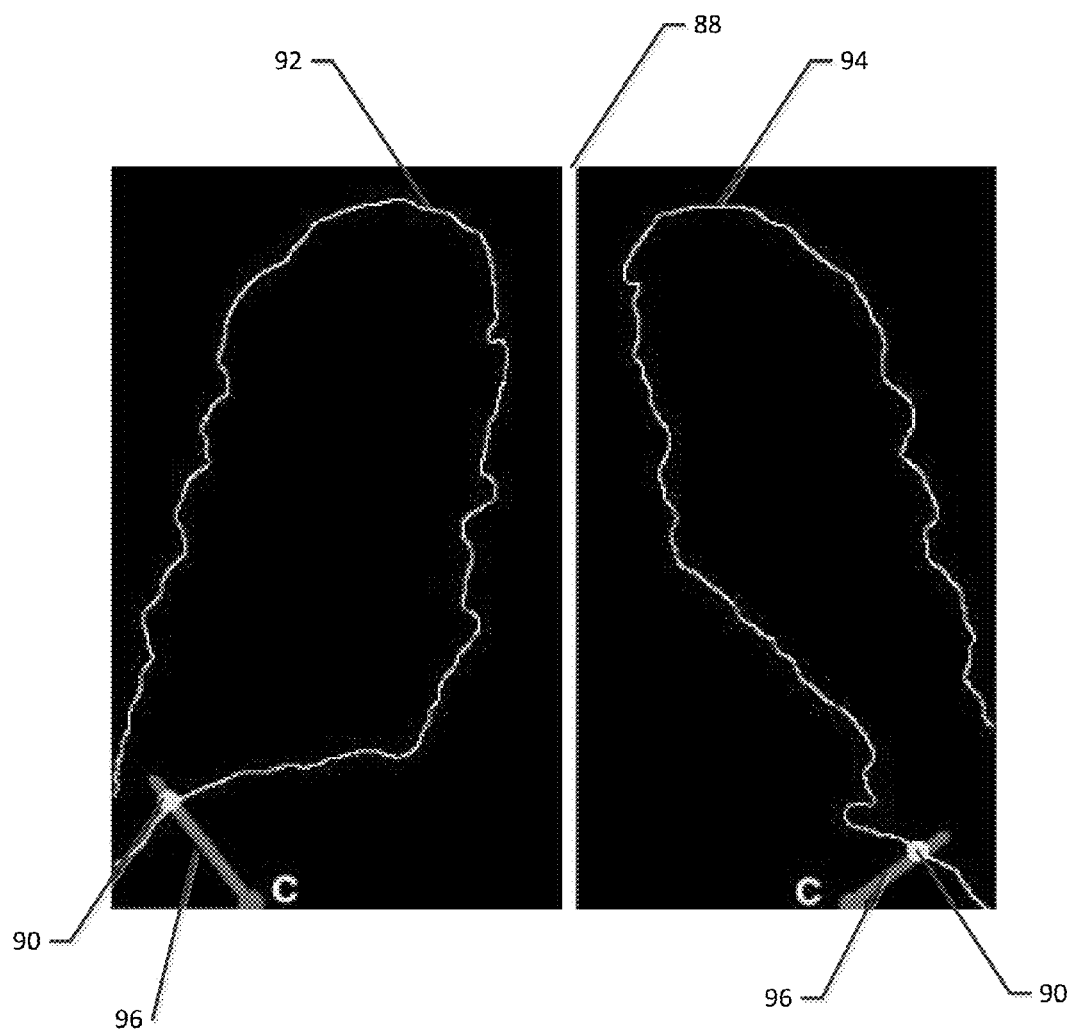
Figure 12:
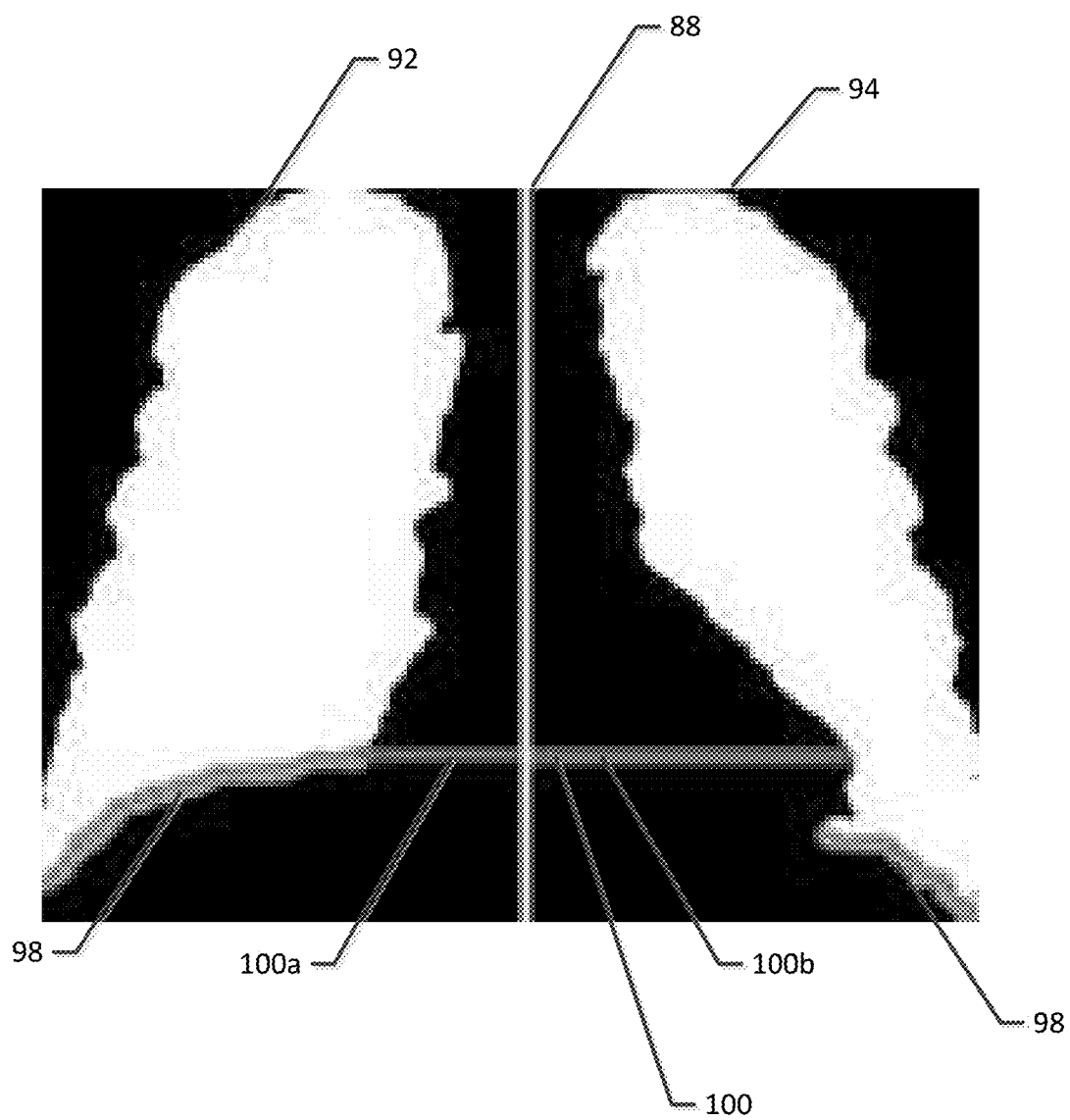
Figure 13:
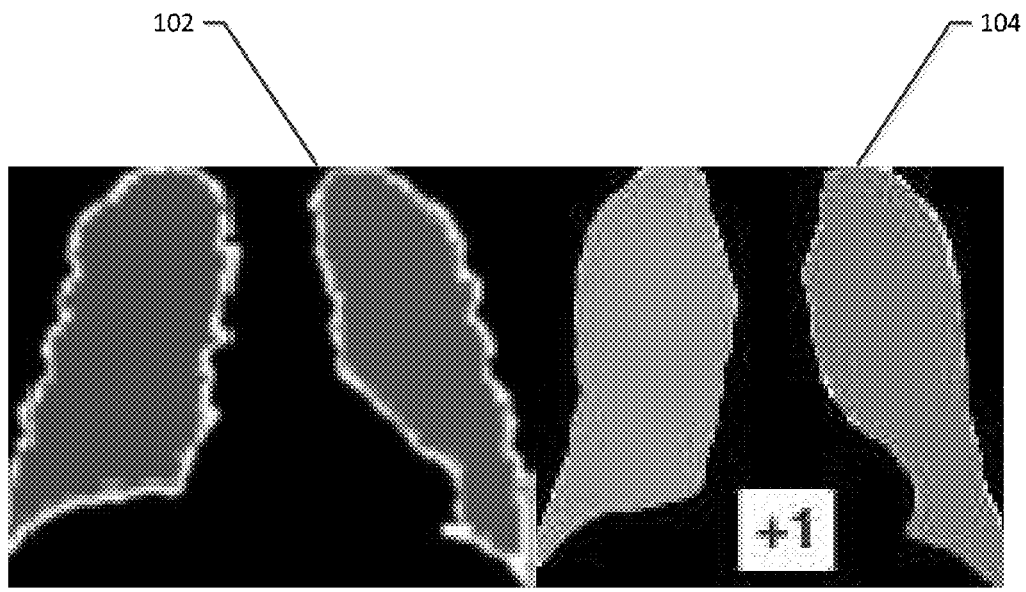
Figure 14:
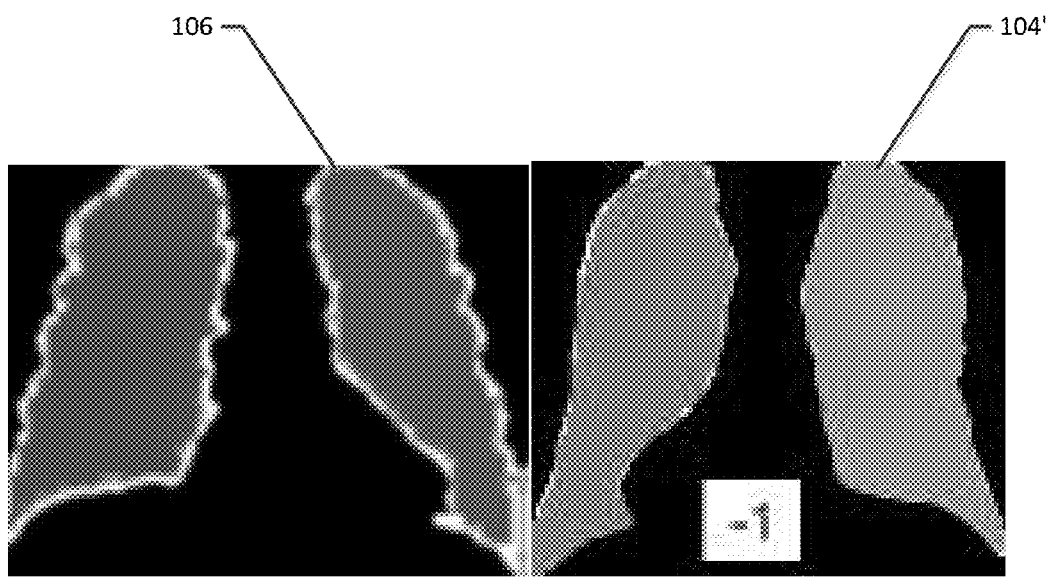

Having thus described aspects of the present disclosure in general terms, reference will now be made to the accompanying drawings, which are not necessarily drawn to scale, and wherein:

FIG. 1 is a block diagram of a system including a PACS viewer configured to receive images captured by a plurality of imaging modalities;

FIG. 2 is a block diagram of a PACS viewer that may be specifically configured in accordance with an example embodiment of the present invention;

FIG. 3 is a flowchart illustrating operations performed, such as by the PACS viewer of FIG. 2, in accordance with an example embodiment of the present invention;

FIG. 4 is an image of a template in accordance with an example embodiment of the present invention;

FIG. 5 is an image in which a plurality of lines have been defined that extend thereacross in accordance with an example embodiment of the present invention;

FIG. 6 is a graphical representation of the pixel values along a respective line depicted in FIG. 5;

FIG. 7 is an image in which seed points are defined along each of the lines and a representative seed point is determined from among the plurality of seed points in accordance with an example embodiment of the present invention;

FIG. 8 is a mask constructed using the representative seed points in accordance with an example embodiment of the present invention;

FIG. 9 is a binary image generated by application of an active contour model in accordance with an example embodiment of the present invention;

FIG. 10 is a binary image following post-segmentation processing in accordance with an example embodiment of the present invention;

FIG. 11 depicts a technique for identifying the diaphragm associated with the left and right lungs in accordance with an example embodiment of the present invention;

FIG. 12 is a binary image in which the left and right lungs are identified based upon a line defined by the diaphragm of one of the lungs in accordance with an example embodiment of the present invention;

FIG. 13 is a graphical representation of a comparison of the binary image and the template in accordance with an example embodiment of the present invention; and FIG. 14 is a graphical representation of a comparison of the binary image and a mirrored version of the template in accordance with an example embodiment of the present invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

A method, computing device and computer program product are provided in accordance with an example embodiment of the present invention in order to determine patient orientation at the time of that an image of a portion of the patient is captured. The image may be a medical image, such as an image of a patient. The image may have been captured by any of a wide variety of different modalities, such as CT, MRI, CR, DR, MG or the like. The image may be utilized for a wide variety of different purposes including diagnosis, treatment, training or the like. Still further, in an instance in which the image is an image of a portion of a patient, the image may be of any of a wide variety of different portions of the patient, such as a limb, organ or the like. For purposes of explanation, however, an image of the patient's chest showing the left and right lungs of the patient will be hereinafter discussed.

By way of example, FIG. 1 illustrates a system 20 that may benefit from an example embodiment of the present invention. As shown, the system includes one or more imaging modalities (three example modalities being shown as modalities 22a, 22b and 22c) for acquiring an image, such as an image of the human body or parts of the human body for clinical purposes such as examination, diagnosis and/or treatment. Examples of suitable modalities include, for example, CT, MRI, CR, DR, MG or the like. The system also includes a PACS server 26 for receiving and processing the image studies from one or more of the imaging modalities and for storing the image studies, such as in image storage 28. The system of FIG. 1 further includes a viewing station, such as a PACS viewer 24, configured to receive an image study from the PACS server, and present the images of the image study such as for review by a medical professional such as a radiologist.

The imaging modalities 22, the PACS viewer 24, the PACS server 26 and/or the image storage 28 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G, 4G or Long Term Evolution (LTE) communication techniques, local area network (LAN), wireless LAN (WLAN) techniques or the like. In accordance with various ones of these techniques, the imaging modality, the PACS viewer, the PACS server and/or the image storage can be coupled to and configured to communicate across one or more networks. The network(s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the imaging modality, viewing station and/or computing apparatus.

The PACS viewer 24 of an example embodiment is embodied by computing device, such as a computer workstation, a personal computer, a tablet computer, a laptop computer, a mobile terminal, e.g., a smartphone, or other type of computing device that includes or is associated with both a display and the processing circuitry for performing the various functions described hereinafter. The computing device of a PACS viewer 24 in accordance with an example embodiment is depicted in FIG. 2. As shown, the PACS viewer includes or is associated and in communication with processing circuitry 32 that is configurable to perform functions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 32 includes a processor 34 and, in some embodiments, such as that illustrated in FIG. 3, further includes memory 36. The processing circuitry may be in communication with or otherwise control a user interface 38, such as a display, a touchscreen, a touch surface, a keyboard and/or other input/output mechanisms and, in some embodiments, may also optionally include a communication interface 39 for communicating with other computing systems. As such, the processing circuitry may be embodied as a circuit chip (e.g., an integrated circuit chip) configured (e.g., with hardware, software or a combination of hardware and software) to perform operations described herein.

The processor 34 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device as described herein. The plurality of processors may be embodied on a single computing device or distributed across a plurality of computing devices collectively configured to function as the computing device. In some example embodiments, the processor may be configured to execute instructions stored in the memory 36 or otherwise accessible to the processor. As such, whether configured by hardware or by a combination of hardware and software, the processor may represent an entity (e.g., physically embodied in circuitry—in the form of processing circuitry 32) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

The processing circuitry 32 may also include memory 36 as shown in FIG. 3. In some example embodiments, the memory may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device. The memory may be configured to store information, data, applications, instructions and/or the like for enabling the computing device to carry out various functions in accordance with one or more example embodiments. For example, the memory may be configured to buffer input data for processing by the processor 34. Additionally or alternatively, the memory may be configured to store instructions for execution by the processor. As yet another alternative, the memory may include one or more databases that may store a variety of files, contents or data sets, such as medical images, e.g., image studies, for a plurality of patients. Among the contents of the memory, applications may be stored for execution by the processor in order to carry out the functionality associated with each respective application. In some cases, the memory may be in communication with one or more of the processor or the user interface 38 via a bus or buses for passing information among components of the computing device.

In addition to the processing circuitry 32, the PACS viewer 24 may include a user interface 38 for displaying and/or receiving data, content or the like. The user interface may include one or more earphones and/or speakers, a display, and/or a user input interface. The user interface, in turn, can include any of a number of devices allowing the computing device to receive data from a user, such as a microphone, a keypad, a touch-sensitive surface (integral or separate from the monitor), a joystick, or other input device. As will be appreciated, the processing circuitry may be directly connected to other components of the computing device, or may be connected via suitable hardware. In one example, the processing circuitry may be connected to the user interface via an adapter configured to permit the processing circuitry to send graphical information to the user interface.

The PACS viewer 24 of an example embodiment may also include a communication interface 39 that may be any means such as a device or circuitry embodied in either hardware or a combination of hardware and software that is configured to receive and/or transmit data from/to other electronic devices in communication with the apparatus, such as by being configured to receive medical image studies from the PACS server 26. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication.

Having now described a PACS viewer 24 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Referring now to FIG. 3, the operations performed, such as by the PACS viewer 24 of FIG. 2, in order to determine patient orientation at the time that an image of a portion of the patient is captured are illustrated in accordance with an example embodiment of the present invention. As shown in block 40, the PACS viewer of an example embodiment includes means, such as the processing circuitry 32, the processor 34 or the like, for registering an image onto a template. The image may be registered onto the template by an iterative process in which affine transformation parameters (translation, rotation and scaling parameters) are updated based on step gradient descent and Mattes mutual information optimization techniques. By registering the image onto a template, background and other unwanted regions of the image may be removed and the image may be straightened so as to facilitate subsequent processing. By way of example, x-ray images of a patient's chest may include regions, such as shoulders or external backgrounds, that are unwanted during an analysis of the patient's lungs. As such, registration of the image unto the template may remove these unwanted regions. Additionally, in some x-ray images, the spine may be slanted to one side rather than being upright with the slanting of the spine potentially causing issues in the subsequent processing of the image. Thus, the registration of the image to the template may straighten the image.

The image to be registered in an image of a patient that has been captured by an image modality, such as a two dimensional projection image captured by a computed radiography modality or a digital radiography modality. The image is typically provided by a PACS server 26 and may be one of a plurality of images provided as an image study. In addition to the images themselves, an image study generally includes additional information, such as may be provided by a header, regarding the image study and the respective images. Among other information, the header of an image study may include information identifying the orientation of the patient at the time that the images of the image study were captured. In this regard, the indication provided by the header may be based upon a predefined protocol in which the patient is presumed to have been in a predefined orientation at the time that the images were captured.

The template is an intensity template image of the same portion of the patient's body that is represented by the images received from the PACS server 26. By way of example, the image to be registered to the template may an image of the patient's chest so as to show the patient's left and right lungs. This template may be constructed in various manners, but it is generally an unbiased anatomical template. In one example, a plurality of images of various patients' chests are processed and combined to generate the template. For example, a plurality of chest x-rays may be cropped around the lungs, the cropped images may be added and an average image may then be obtained. The plurality of images may then be registered onto the average image, one at a time. The average of the registered images may then define the template.

The PACS viewer 24 of an example embodiment also includes means, such as the processing circuitry 32, the processor 34 or the like, for determining a representative seed point within each of the left and right lungs as represented by the image, typically following registration onto a template. See block 42 of FIG. 3. In order to determine the seed points inside the left and right lungs as represented by the image, the image may initially be inverted, in terms of the gray scale values of the pixels that comprise the image, such that the lungs appear darker than the remainder of the patient's chest. The processing circuitry of this example embodiment is then configured to define a plurality of lines 60 extending across the image, such as plurality of horizontal lines as shown in FIG. 5. Although shown to extend horizontally, the lines may extend in other directions so long as the lines pass through both the lungs as represented by the image.

The intensity of the pixels of the image along a line 60 varies depending upon the gray scale level associated with the respective pixels. For Monochrome 2 images in which the smallest pixel value is displayed as fully black and the largest pixel value is displayed as fully black, the greater intensity values are associated with those regions outside of the lungs as those regions are shown with a lighter color and smaller intensity values within the lungs as the lungs are shown in a darker color. In this regard, FIG. 6 graphically depicts the intensity values along a line that extends across the left and right lungs as representative by the image. Other types of images may differently represent the pixel values such that FIG. 6 is shown by way of example, but not of limitation. For example, a Monochrome 1 image causes a pixel having the smallest value to be displayed as fully white and a pixel having the largest value to be displayed as fully black. This results in the intensity of the pixels of the image along line 60 in a Monochrome 1 image being the inverse of what is shown in FIG. 6. Local maxima in a Monochrome 2 image will be local minima in a Monochrome 1 image and vice versa. As a point of comparison, in an instance in which the Monochrome 1 and Monochrome 2 images of a lung are represented by ten bits which results in a maximum value of 4095, the pixel values of the lung in one example of a Monochrome 2 image may be in the range of 20-50, while the pixel values of the lung in one example of a Monochrome 1 image may be in a corresponding range of (4095−50=4045) to (4095−20=4075). The following discussion will be based upon a Monochrome 2 image, but other types of images may alternatively be utilized as described above with the reliance upon the Monochrome 2 image being by way of example, but not of limitation. In order to obtain a smoother curve of the intensity values along a line across the lungs, the processing circuitry 32 of an example embodiment is configured to determine the average intensity of the pixels along a respective line and to then fit a Fourier model, such as an eight-term Fourier model, to the pixel values along the respective line.

As shown, the processing circuitry 32 of an example embodiment is configured to identify both local maxima 62, 66, 70 and 74 and local minima 64, 68 and 72 from among the pixels values along a respective line 60 across the lungs. The processing circuitry of this example embodiment then identifies the two widest troughs 76, 78 of the graph that include a local minima to correspond to the left and right lungs. Further, the processing circuitry of this example embodiment identifies the local minima within each trough along a respective line to be a seed point. Thus, along a respective line, one seed point is generally defined within the left lung and another seed point is generally defined within the right lung with each of the seed points representing a local minima within one of the two widest troughs along the respective line. The processing circuitry of an example embodiment is configured to repeat this procedure along each of the lines that extend across the image so as to determine seed points 80 on each of the plurality of lines within each of the left and right lungs, as shown in FIG. 7.

The processing circuitry 32 of this example embodiment is also configured to determine a representative seed point 82 within each of the left and right lungs from among these seed points 80 determined on each of the plurality of lines 60. By way of example, the processing circuitry of an example embodiment is configured to determine the median of the seed points within the left lung and the median of the seed points within the right lung. For example, FIG. 7 depicts each of the seed points identified along the lines that extends across the image as well as the representative seed points within the left and right lungs as determined by the medians of the seed points with a respectable lung. As also shown in FIG. 7, the processing circuitry of an example embodiment is configured to define a region, such as a square-shaped region, around each representative seed point. The region may have a predefined size.

In block 44 of FIG. 3, the PACS viewer 24 of an example embodiment also include means, such as the processing circuitry 32, the processor 34 or the like, for subjecting the image to anisotropic diffusion prior to applying an active contour model, as described below. In this regard, anisotropic diffusion reduces image noise without removing significant parts of the image content, such as edges, lines or other details that are important for the interpretation of the image. As such, anisotropic diffusion is able to blur the image so as to smooth the sharp edges of the ribs that may otherwise cause difficulties during subsequent processing of the image. Although, anisotropic diffusion maybe applied in various manners, the processing circuitry of an example embodiment is configured to subject the image to an isotropic diffusion by convolving the image with the two-dimensional isotropic Gaussian filter.

The PACS viewer 24 of an example embodiment also includes means, such as the processing circuitry 32, the processor 34 the like, for applying an active contour model to each of the left and right lungs as represented by the image, such as the image following anisotropic diffusion, so as to generate a binary image, such as an image formed solely from black and white pixels as opposed to an image including pixels having a variety of gray levels. See block 46 of FIG. 3. In order to apply the active contour model, the processing circuitry of an example embodiment is configured to initialize the active contour model with a mask constructed using the representative seed points 82. As shown in FIG. 8, the mask of an example embodiment is a black image that includes two white regions 84 that correspond to the regions defined about the representative seed points. In this regard, the mask of the illustrated embodiment includes two white squares that are centered upon the representative seed points in the left and right lungs.

To ensure that the left and right lungs are segmented as two distinct objects, the processing circuitry 32 of an example embodiment is configured to determine, for each line 60, the average of the seed points 80 in the left and right lungs along the respective line across the image. The processing circuitry of this example embodiment then defines a midline based upon the average value of the seed points along each line. For example, the midline may be defined so as to extend through the average value of the seed points along each line or the midline may be defined as a best fit line through the average value of the seed points along each line. As such, the image is divided into two portions by the midline and the processing circuitry is then configured to separately apply the active contour model to each portion of the image. As known to those skilled in the art, an active contour model is a seeded region-growing algorithm that provides pixel-based image segmentation. The active contour model examines neighboring pixels of an initial seed point and determines which, if any, of the neighboring pixels should be added to the region. The process is then applied iteratively. In the embodiment in which a mask as shown in FIG. 8 is applied to an image, the processing circuitry applies the active contour model to each portion of the image by beginning at a respective white region 84 of the mask indicative of the representative seed point 82. The active contour model then iteratively considers neighboring pixels until a point is reached that the energy of the control points that make up the active contour model is minimized with the active contour model then being halted. The active contour model of an example embodiment has two terms, one term relating to the internal energy that describes the smoothness of the curve and another term relating to the external energy that may be determined based on the gradient of the image, the edge magnitude, texture or intensity. As such, the active contour model may iteratively consider neighboring pixels until a point is reached that the internal and external energy of the control points that make up the active contour model is minimized. In this example embodiment, the optimal energy state of the active contour model is obtained in an instance in which the contour is wrapped around the desired object, that is, the lung within the respective portion of the image. FIG. 9 illustrates an example binary image of the left and right lungs that is obtained following application of the active contour model.

Following the segmentation of the left and right lungs and the application of the active contour model which results in a binary image, such as shown in FIG. 9, the processing circuitry 32 of an example embodiment is configured to remove all falsely detected objects outside of the lung regions and to fill the black holes within the white lung regions. For example, the black regions in the otherwise white lungs of this example embodiment may be identified based upon their location within the lung contours and/or their size relative to the surrounding white region, and a morphological operation, such as a hole filling routine, may be utilized to fill the black regions with white pixels consistent with the remainder of the lungs in this example. Additionally, the processing circuitry of an example embodiment is configured to perform morphological closing to reconnect any separated portions of the lungs in the binary image. In an example embodiment, processing circuitry is also configured to insure separation of the lungs in the binary image by placing a thin black vertical rectangle upon the midline. Further, the processing circuitry of an example embodiment is configured crop the binary image around the lungs, thereby creating a binary image of the type depicted in FIG. 10.

The processing circuitry 32 of an example embodiment is also configured to insure that the left and right lungs have been adequately segmented in the binary image prior to further analyzing binary image. For example, processing circuitry of an example embodiment is configured to determine the normalized cross correlation of the segmented binary image and the template. If the result fails to satisfy a threshold, such as by being less than a predefined similarity threshold, the segmentation is not considered adequate and further processing of the respective binary image may be halted. However, if the result satisfies the threshold, such as by exceeding the predefined similarity threshold, the left and right lungs of the binary image may be considered adequately segmented and further analysis of the binary image may be performed.

The PACS viewer 24 of an example embodiment also includes means, such as the processing circuitry 32, the processor 34 or the like, for detecting a least one feature from the binary image to permit identification of the left and right lungs, such as to identify which of the lungs is the left lung and which of the lungs is the right lung. See block 48 of FIG. 3. The feature detection may be performed in various manners. In an example embodiment, the processing circuitry is configured to detect a feature from the binary image by determine the area of the left lung and the area of the right lung from the binary image. The processing circuitry of this example embodiment is also configured to identify the right lung as the lung within the binary image having the larger area. As such, the left lung is correspondingly identified as the lungs within the binary image having the smaller area.

In another example embodiment, the processing circuitry 32 is configured to determine the location the heart. As the heart is most often on left side of the patient's chest, the identification of the location the heart correspondingly permits the left lung to be identified as the lung in the binary image that is closest to the location of the heart. Similarly, the right lung may be identified as the lung within the binary image that is furthest from the location of the heart. In order to locate the heart, the processing circuitry of an example embodiment is configured to define a line between the left and right lungs as represented by the binary image. The line is located based upon a diaphragm of one of the lungs.

In this regard, the processing circuitry 32 is initially configured to detect the diaphragms. In order to detect the diaphragms, the processing circuitry is again configured to divide the binary image into two portions 92, 94 separated, for example, by the midline 88 between the left and right lungs. The processing circuitry of this example embodiment is then configured to define a horizontal line segment along the lower edge of each portion of the binary image. Each line segment 96 is then rotated as shown in FIG. 11, such as from 0° to 180°, about the center of rotation c where c is defined as c=(¼*binary image width, binary image height). As a result of the rotation of each line segment, the points of intersections 90 of the rotated line segment and the edge of the lung within the respective portion of the binary image are identified and the associated error is determined and minimized. These intersection points are considered points along the diaphragm, e.g., diaphragm points. In order to identify these diaphragm points, each line segment is rotated through an angular range, e.g., 0° to 180°, and at each of a plurality of angular positions within the angular range, the edge points of the lung that are intersected by the line segment are initially detected and the point closest to the center of rotation c of the line segment (if there is more than one edge point identified at the respective angular position) is then considered to be a diaphragm point. This process is repeated for all angular positions within the angular range for each line segment and corresponding diaphragm points are identified. The diaphragm points, in turn, define the diaphragm associated with a respective lung. From among the set of diaphragm points identified for a respective lung, the processing circuitry is then configured to determine the inner corner of each diaphragm, that is, the inner corner of the diaphragm identified in each portion of the binary image. In this regard, the inner corner of the diaphragm is the point identified as the diaphragm that is closest to the midline.

The processing circuitry 32 of this example embodiment is then configured to define a line 100 that extends between the left and right lungs and that is located based upon a diaphragm 98 of one of the lungs. As shown in FIG. 12, the line is defined so as to extend horizontally between the left and right lungs from the inner corner of the higher diaphragm, that is, the diaphragm that is spaced further from the lower edge of the binary image. The line defined between the left and right lungs as represented by the binary image is then divided in the first and second lines segments 100a, 100b by the midline 88 that extends between the left and right lungs. Each line segment extends from the midline to a respective lung. The processing circuitry of this example embodiment is configured to compare the length of each of the first and second line segments. Thereafter, the processing circuitry is configured to identify the left lung to be on the same side of the midline of the binary image as the longer of the first and second line segments. Correspondently, the right lung is on the same side of the midline as the shorter of the first and second line segments.

In a further example embodiment, the processing circuitry 32 is configured to discriminate between the left and right lungs within the binary image by making a first comparison of the binary image to the template and a second comparison of a mirrored version of one of the binary image or the template to the other one of the binary image or the template. The mirrored version of the binary image or the template is a mirrored version taken about the midline 88 between the left and right lungs. For example, the binary image may be separately compared to the template and to a mirrored version of the template. By way of example, FIG. 13 depicts a binary image 102 and the template 104 (designated +1) that may be compared, while FIG. 14 depicts the same binary image 102 and a mirrored version of the template 104', designated −1.

The processing circuitry 32 of this example embodiment is configured to determine which of the first comparison or the second comparison is indicative of more similarity, such as by determining one of the template 104 or the mirrored image of the template 104' that is most similar to the binary image 102. The processing circuitry may determine similarity in a various manners, but the processing circuitry of an example embodiment determines the normalized cross correlation between the binary image and the template to determine a similarity coefficient between and also determines the normalized cross correlation between the binary image and the mirrored version of the template to determine another similarity coefficient. The processing circuitry of this example embodiment is also configured to identify the left and right lungs within the binary image based upon the predefined orientation of the template and the one of the first or second comparison that is indicative of more similarity. In the embodiment in which the processing circuitry determines the similarity coefficient for each of the template and a mirrored version of the template, such as based upon the normalized cross correlation with the binary image, the processing circuitry is configured to identify the respective one of the template or the mirrored version of the template that has the larger similarity coefficient to have the same orientation as the binary image. As the template has a predefined orientation such that the relative positions of left and right lungs within the template are known to be on the left and right sides, or vice versa, the determination of which of the template of the mirrored version of the template is most similar to the binary image permits the processing circuitry to also determine the orientation of the left and right lungs within the binary image.

Based upon the identification of the left and right lungs within the binary image, the processing circuitry 32 is configured to predict the patient orientation at the time that the image was captured. The processing circuitry of an example embodiment is configured to notify the user, such as a radiologist, of the predicted orientation of the patient at the time that the image was captured. In another embodiment, however, the PACS server 24 includes means, such as the processing circuitry, the processor 34 or the like, for comparing the patient orientation that has predicted based upon the foregoing analysis of the image to the indication of orientation that is associated with the image, such as the indication of orientation that is provided in the header associated with the image study. See block 52 of FIG. 3. In this example embodiment, the PACS server also includes means, such as the processing circuitry, the processor, the user interface 38 or the like, for causing a notification to be provided in an instance in which the patient orientation as predicted is different than the indication of orientation that is associated with the image. See block 54 of FIG. 3. As such, a user may then resolve the difference by personally reviewing the image so as to determine the actual orientation of the image before proceeding with recommendations regarding the treatment of the patient.

In an example embodiment, the PACS viewer 24 includes means, such as the processing circuitry 32, the processor 34 or the like, for predicting patient orientation based upon the identification of the left and right lungs utilizing a support vector machine classifier. See block 50 of FIG. 3. In this regard, the predicted orientation of the patient may be determined by plurality of feature detection techniques, such as based upon the area of the lungs, the location of the heart and/or the similarity of the binary image to a template of a predefined orientation. The processing circuitry of this example embodiment is configured to implement a support vector machine classifier that considers the prediction of patient orientation from each of the different feature detection techniques and then predicts the patient orientation based thereupon. The prediction of patient orientation by a support vector machine classifier may be particularly useful in an instance in which the predictions of patient orientation as determined by a plurality of feature detection techniques are not consistent with one another.

In an embodiment in which the processing circuitry 32 implements the support vector machine classifier, support vector machine classifier of an example embodiment may utilize a Gaussian radial basis function (RBF) as follows:

$$K(x_i, x_j) = e^{-(\gamma \|x_i - x_j\|^2)}, \gamma > 0$$

wherein $x_i$ is a support vector and $x_j$ is a test data point. The support vectors and the test data points may be defined in various manners. For example, the available data consisting of m+n samples may be divided into m samples that serve as support vectors and n samples that serve as test samples. Additionally or alternatively, support vectors may be defined by initially clustering the available data and then utilizing cluster centers as support vectors. The RBF kernel has two parameters, γ and C>0 with unknown values beforehand. To determine the optimal (γ, C), the processing circuitry of an example embodiment is configured to perform a grid search with exponentially growing sequences of C and γ, such as $C \in \{2^{-5}, 2^{-3}, \ldots, 2^{13}, 2^{15}\}$; $\gamma \in \{2^{-15}, 2^{-13}, \ldots, 2^{1}, 2^{3}\}$. Typically, each combination of parameter choices is checked using cross validation and the parameters with the best cross-validation accuracy are selected.

The support vector machine classifier may be trained with a plurality of images. The plurality of the images include a first set of images that are such that when subjected to a plurality of feature detection techniques cause the patient orientation to be unanimously predicted as the same first orientation, designated +1. The plurality of the images also include a second set of images that are such that when subjected to the plurality of feature detection techniques cause the patient orientation to be unanimously predicted as the same second orientation, designated −1 (typically the opposite orientation from the first orientation). Once trained, the support vector machine classifier as implemented by the processing circuitry 32 of an example embodiment is configured to consider the prediction of patient orientation from each of the different feature detection techniques and to then predict the patient orientation based thereupon.

A PACS viewer 24 and an associated method and computer program product are provided in accordance with an example embodiment for identifying patient orientation in a reliable and automated manner. For example, the PACS viewer and associated method and computer program product of an example embodiment are configured to discriminate between the left and right lungs of a patient based upon an image of the patient without reliance upon placement of a designation proximate the patient at the time that the image was captured, burning a designation into an image or orientation of the patient at the time of image capture according to a predefined protocol. As such, the PACS viewer and associated method and computer program product offer reliable identification of the left and right lungs of a patient while providing greater freedom in terms of the orientation of the patient at the time that the image is captured.

As described above, FIG. 3 is a flowchart of a method, computing device 30 and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 36 of a computing device and executed by processing circuitry 32 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 32 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A Picture Archiving and Communications System (PACS) viewer comprising processing circuitry configured to:
    register an image onto a template;
    determine a representative seed point within each of left and right lungs as represented by the image;
    apply an active contour model to each of the left and right lungs to generate a binary image of the left and right lungs, wherein the processing circuitry is configured to apply the active contour model by initializing the active contour model with a mask constructed using the representative seed points; and
    detect at least one feature from the binary image to permit identification of the left and right lungs.

2. A PACS viewer according to claim 1 wherein the processing circuitry is configured to detect at least one feature from the binary image by:
    determining an area of the left and right lungs from the binary image; and
    identifying the right lung to have the larger area.

3. A PACS viewer according to claim 1 wherein the processing circuitry is configured to detect at least one feature from the binary image by:
    defining a line between the left and right lungs as represented by the binary image, wherein the line is located based upon a diaphragm of one of the lungs;
    dividing the line into first and second line segments extending between a midline between the left and right lungs and a respective lung;
    comparing a length of each of the first and second line segments; and
    identifying the left lung to be on the same side of the midline as the longer of the first and second line segments.

4. A PACS viewer according to claim 1 wherein the processing circuitry is configured to detect at least one feature from the binary image by:
    making a first comparison of the binary image to the template and making a second comparison of a mirrored version of one of the binary image or the template to the other one of the binary image or the template, wherein the template represents a predefined orientation with respect to the left and right lungs;
    determining which of the first comparison or the second comparison is indicative of more similarity; and
    identifying the left and right lungs within the binary image based upon the predefined orientation of the template and the one of the first or second comparison that is indicative of more similarity.

5. A PACS viewer according to claim 1 wherein the processing circuitry is configured to determine a representative seed point by:
    defining a plurality of lines extending across the image;
    within each of the left and right lungs, determining a seed point on each of the plurality of lines; and
    determining the representative seed point within each of the left and right lungs from among the seed points determined on each of the plurality of lines within each of the left and right lungs.

6. A PACS viewer according to claim 1 wherein the processing circuitry is further configured to subject the image to anisotropic diffusion prior to applying the active contour model.

7. A PACS viewer according to claim 1 wherein the processing circuitry is further configured to predict patient orientation based upon the identification of the left and right lungs utilizing a support vector machine classifier.

8. A PACS viewer according to claim 7 wherein the processing circuitry is further configured to:
    compare the patient orientation that is predicted to an indication of orientation that is associated with the image; and cause a notification to be provided in an instance in which the patient orientation that is predicted is different than the indication of orientation that is associated with the image.

9. A method for identifying patient orientation, the method comprising:
registering an image onto a template;
determining a representative seed point within each of left and right lungs as represented by the image;
applying an active contour model to each of the left and right lungs to generate a binary image of the left and right lungs, wherein applying the active contour model comprises initializing the active contour model with a mask constructed using the representative seed points; and
detecting at least one feature from the binary image to permit identification of the left and right lungs.

10. A method according to claim 9 wherein detecting at least one feature from the binary image comprises:
determining an area of the left and right lungs from the binary image; and
identifying the right lung to have the larger area.

11. A method according to claim 9 wherein detecting at least one feature from the binary image comprises:
defining a line between the left and right lungs as represented by the binary image, wherein the line is located based upon a diaphragm of one of the lungs;
dividing the line into first and second line segments extending between a midline between the left and right lungs and a respective lung;
comparing a length of each of the first and second line segments; and
identifying the left lung to be on the same side of the midline as the longer of the first and second line segments.

12. A method according to claim 9 wherein detecting at least one feature from the binary image comprises:
making a first comparison of the binary image to the template and making a second comparison of a mirrored version of one of the binary image or the template to the other one of the binary image or the template, wherein the template represents a predefined orientation with respect to the left and right lungs;
determining which of the first comparison or the second comparison is indicative of more similarity; and
identifying the left and right lungs within the binary image based upon the predefined orientation of the template and the one of the first or second comparison that is indicative of more similarity.

13. A method according to claim 9 wherein determining a representative seed point comprises:
defining a plurality of lines extending across the image;
within each of the left and right lungs, determining a seed point on each of the plurality of lines; and
determining the representative seed point within each of the left and right lungs from among the seed points determined on each of the plurality of lines within each of the left and right lungs.

14. A method according to claim 9 further comprising subjecting the image to anisotropic diffusion prior to applying the active contour model.

15. A method according to claim 9 further comprising predicting patient orientation based upon the identification of the left and right lungs utilizing a support vector machine classifier.

16. A method according to claim 15 further comprising:
comparing the patient orientation that is predicted to an indication of orientation that is associated with the image; and
causing a notification to be provided in an instance in which the patient orientation that is predicted is different than the indication of orientation that is associated with the image.

17. A computer program product for identifying patient orientation, the computer program product comprising a non-transitory computer readable storage medium having program code portions stored thereon, the program code portions configured, upon execution, to:
register an image onto a template;
determine a representative seed point within each of left and right lungs as represented by the image;
apply an active contour model to each of the left and right lungs to generate a binary image of the left and right lungs, wherein applying the active contour model comprises initializing the active contour model with a mask constructed using the representative seed points; and
detect at least one feature from the binary image to permit identification of the left and right lungs.

18. A computer program product according to claim 17 wherein the program code portions configured to detect at least one feature from the binary image comprise program code portions configured to:
determine an area of the left and right lungs from the binary image; and
identify the right lung to have the larger area.

19. A computer program product according to claim 17 wherein the program code portions configured to detect at least one feature from the binary image comprise program code portions configured to:
define a line between the left and right lungs as represented by the binary image, wherein the line is located based upon a diaphragm of one of the lungs;
divide the line into first and second line segments extending between a midline between the left and right lungs and a respective lung;
compare a length of each of the first and second line segments; and
identify the left lung to be on the same side of the midline as the longer of the first and second line segments.

20. A computer program product according to claim 17 wherein the program code portions configured to detect at least one feature from the binary image comprise program code portions configured to:
make a first comparison of the binary image to the template and making a second comparison of a mirrored version of one of the binary image or the template to the other one of the binary image or the template, wherein the template represents a predefined orientation with respect to the left and right lungs;
determine which of the first comparison or the second comparison is indicative of more similarity; and
identify the left and right lungs within the binary image based upon the predefined orientation of the template and the one of the first or second comparison that is indicative of more similarity.

* * * * *